United States Patent [19]

Takenouti et al.

[11] 4,412,346
[45] Oct. 25, 1983

[54] X-RAY PHOTOGRAPHY APPARATUS

[75] Inventors: Eisuke Takenouti, Yamato; Sigeru Urata, Tochigi, both of Japan

[73] Assignee: Tokyo Shibaura Denki Kabushiki Kaisha, Kawasaki, Japan

[21] Appl. No.: 399,868

[22] Filed: Jul. 19, 1982

[30] Foreign Application Priority Data

Jul. 21, 1981 [JP] Japan .............................. 56-114982

[51] Int. Cl.³ ........................ G01N 21/26; G01J 3/34; G03B 41/16
[52] U.S. Cl. .................................... 378/181; 378/190
[58] Field of Search ............... 378/190, 197, 181, 196, 378/62

[56] References Cited

U.S. PATENT DOCUMENTS 2,831,123  4/1958  Daly ................................. 378/190
3,892,967  7/1975  Grady et al. ...................... 378/197

Primary Examiner—Alfred E. Smith
Assistant Examiner—T. N. Grigsby
Attorney, Agent, or Firm—Cushman, Darby & Cushman

[57] ABSTRACT

In an X-ray photography apparatus of this invention, an X-ray tube and an image receiving device are attached to two tilting members which are each rockably supported on the distal end portion of a traveling support frame telescopically protruding parallel to a horizontal main axis from a rotating base rotating about the main axis. The position and the angle of X-raying of the X-ray tube may be set as desired by suitably selecting the length of extension of the traveling support frames and the angle of rotation of the tilting members. It is also possible to set as desired the position and direction of an image receiving device for receiving an X-ray beam transmitted through a subject or a patient.

7 Claims, 25 Drawing Figures

X-RAY PHOTOGRAPHY APPARATUS

BACKGROUND OF THE INVENTION

This invention relates to an X-ray photography apparatus used for X-ray diagnosis, more specifically to an X-ray photography apparatus used for X-ray diagnosis of the circulatory system.

In an X-ray diagnosis of the circulatory system, it is necessary to photograph X-ray images of blood vessels distributed over a widge range covering substantially all parts or regions of a subject or a patient, including the heart, coronary arteries, brain, abdominal region, lower limbs, etc. In the photographing or filming, the patient must be X-rayed along the course best suited for the diagnosis, and an image receiving device need be positioned and oriented in an optimum manner. An X-ray diagnosis of blood vessels of the heart, for example, requires the use of a first photographing method or cross-directional photographing method and a second photographing method or longitudinal directional photographing method. In the first photographing method, X-rays are projected on the part of the patient to be photographed or filmed on a cross direction normal to the body axis of the patient, in various directions, i.e., in frontal, lateral and many oblique directions. In the second photographing method, X-rays are projected on a longitudinal direction containing the body axis of the patient in the direction substantially normal to the body axis and in many other directions at angles to the normal direction. The cerebral artery, such as the carotid, is photographed from the front of the patient by a third photographing method or Towne method in which an X-ray beam is projected from the forehead side with its central axis at an angle to the orbit metal basal line. To avoid exposure of the crystalline lens, a fourth photographing method has recently been used, in which an X-ray tube is moved to be located under a table carrying a patient and radiates X-rays from under. According to the fourth photographing method, the X-ray must be radiated in the opposite direction to that for the Towne method. In taking an X-ray photograph of blood vessel distributed in the lower limb of a patient, a fifth photographing method is executed in which an X-ray tube and an image receiving device are shifted intermittently in parallel with each other over the lower limb region. In any of the five photographing methods, the image receiving device should naturally be located in a suitable position relative to the course of X-ray radiation.

The photographing X-ray images of the circulatory system positively requires cine-filming for some objects of diagnosis, but needs only the normal direct photographing method for others. The cine-filming is needed in the diagnosis of those parts, such as the heart and the coronary arteries, of which it is quite essential to observe the motion. The cine-filming is performed by using a cinecamera for shooting an X-ray image intensified by an image intensifier (hereinafter referred to as an I-I section). Since the cine-filming need, however, be executed while monitoring the target regions, so it requires the use of a television unit as well as the cinecamera, and the X-ray image delivered from the I-I section is received by a vidicon. The cine-filming is unnecessary for the diagnosis of those blood vessels, such as those of a brain, the abdominal region, the lower limbs, etc., in which blood flows extremely slowly. In this case, direct photographing is often performed with use of a film changer (FC).

Thus, the X-ray photography apparatus used in the diagnosis of the circulatory system is expected to fulfill many requirements as follows. Since the target regions are distributed throughout the whole body of a patient, the X-ray tube and the image receiving device are desired to be moved over a wide range substantially to cover at least the half length of the stature of the patient. Moreover, X-rays need be projected on the target regions via various courses, and the X-ray receiving direction of the image receiving device should be varied with the course of X-ray radiation. Furthermore, the apparatus need be able to switch from the cine-filming to the direct photographing with ease.

These rquirements are attributable to the circumstance that the diagnosis of the circulatory system often requires close attendance of an assistant and the use of various auxiliary appliances or devices, so that the assistant and the auxiliary appliances or devices need be moved along with the patient who is moved between the X-ray tube and the image receiving device to be examined at various parts. Such awkwardness may be eliminated by enabling the X-ray tube and the image receiving device to move over the range substantially to cover at least the half length of the stature of the patient.

Various X-ray photography apparatus have been developed to meet the aforementioned needs. Heretofore, however, no apparatus has been provided yet which can fulfill all those requirements singly. This is so because the conventional apparatus would not be able to control independently the position and X-ray radiating direction of the X-ray tube, as well as the position a direction of the image receiving device, as desired.

SUMMARY OF THE INVENTION

The object of this invention is to provide an X-ray photography apparatus capable of singly executing all of the aforementioned first to fifth photographing methods with ease according to the parts of a subject to be examined and the details of diagnosis.

In order to attain the above object, an X-ray photography apparatus of this invention comprises a rotating body rotatable about a substantially horizontal main axis, an X-ray tube for radiating an X-ray beam along a main plane containing the main axis, an image receiving device for photographing an X-ray image formed after the X-ray beam is transmitted through a subject lying in the path of the X-ray beam, first transfer means capable of supporting the image receiving device in a position off the main axis and moving the image receiving device substantially parallel to the main axis over a range exceeding the half length of the stature of the subject, second transfer means capable of supporting the X-ray tube substantially on the opposite side of the main axis to the image receiving device and moving the X-ray tube substantially parallel to the main axis over a range exceeding the half length of the stature of the subject, first tilting means attached to the first transfer means to change the direction of the image receiving device within the main plane, second tilting means attached to the second transfer means to change the direction of the X-ray tube without the main plane, and a control circuit capable of driving the first and second transfer means and the first and second tilting means to set independently the position and direction of the X-ray tube within the main plane and the position and direction of the image receiving device within the main plane.

By the use of the X-ray photography apparatus of this invention with the aforementioned construction, the first photographing method can be executed by rotating the rotating body, and the second photographing method, as well as the third, fourth and fifth photographing methods, can be performed by selectively operating the first and second transfer means and the first and second tilting means according to the purpose of photographing or filming. Moreover, as the X-ray tube and image receiving device are shifted by means of the first and second transfer means over at least a stroke length longer than half the length of the stature of a patient. As the result provided the table on which a patient is laid is shifted to a suitable position, and X-ray photography usually executed with the catheter inserted from the inguinal region to the heart and X-ray photography of the lower limb region of the patient are performed without removing the table and patient. Thus, the apparatus of this invention may highly conveniently be used for the X-ray diagnosis of the circulatory system.

DETAILED DESCRIPTION OF THE PREFERRED EMBODIMENT

Figure 1:
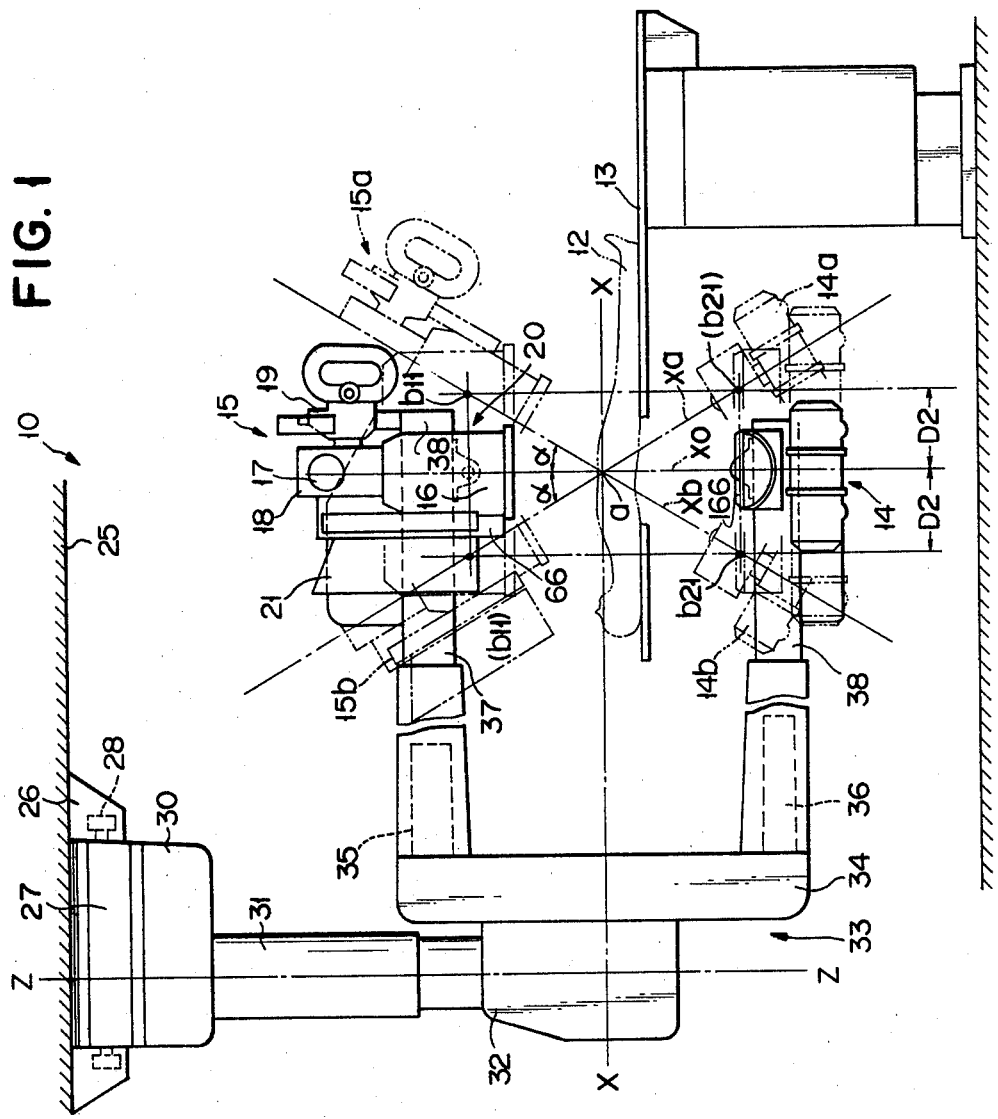
FIG. 1 is a front view of an X-ray photography apparatus of this invention.

There will now be described an X-ray photography apparatus according to an embodiment of this invention. FIG. 1 is a front view showing an outline of the principal part of the X-ray photography apparatus 10. A subject or a patient 12 is laid on a table 13 located between an X-ray tube 14 and an image receiving device 15, and is exposed to X-rays emitted from the X-ray tube 14. The X-rays are received by the image receiving device 15. The image receiving device 15 comprises a cine unit 20 including an image intensifier 16 (hereinafter referred to simply as an I—I section), a television camera 17, an optical system 18 coupling the I—I section 16 and the TV camera 17, and a cinecamera 19 for filming an image from the TV camera 17, and a film changer unit 21 (hereinafter referred to as an FC unit) for directly photographing an X-ray image. Both units 20 and 21 are so set as to be able to receive the X-rays as required. A ceiling 25 is fitted with a pair of guide rails 26 which extend at substantially right angles to the plane of the drawing. A traveling frame 27 can move along the guide rails 26 with the aid of rollers 28 attached to the traveling frame 27. A first rotation mechanism 30 is attached to the lower portion of the traveling frame 27, and a second rotation mechanism 32 is attached to the bottom of the first rotation mechanism 30 by means of an expansion mechanism 31. The second rotation mechanism 32 is driven by the first rotation mechanism 30 to rotate about a vertically extending center line or a vertical axis Z —Z, and can move up and down by the agency of the expansion mechanism 31. A rotating body 33 looking U-shaped in FIG. 1 is driven by the second rotation mechanism 32 to rotate about a substantially horizontally extending center line or a main axis X—X. The rotating body 33 is provided with a base 34 attached to the second rotation mechanism 32, and first and second arms 35 and 36 extending substantially parallel to the main axis X—X of the base 34 at distances therefrom. A first traveling support frame 37 is coupled to the first arm 35 so as to be able to move along the main axis X—X, thus forming a first expansion tube member. Likewise, a second traveling support frame 38 is coupled to the second arm 36 so as to be able to move along the main axis X—X, thus forming a second expansion tube member. The image receiving device 15 and the X-ray tube 14 are mounted on the first and second traveling support frames 37 and 38, respectively. The image receiving device 15 can move not only together with the first traveling support frame 37 along the main axis X—X, but also relatively to the frame 37. Likewise, the X-ray tube 14 can move not only together with the second traveling support frame 38, but also relatively to the frame 38. With such construction, X-rays from various directions can be applied to the patient 12 on the table 13, and received. The mechanisms and operations to move the X-ray tube 14 and the image receiving device 15 in the aforesaid manner will later be described in detail. The X-rays emitted from the X-ray tube 14 advance along a main plane containing the main axis X—X, and are received by the cine unit 20 or the FC unit 21 included in the image receiving device 15. The movement of the cine unit 20 or the FC unit 21 to the position for the reception of X-rays is induced by a conversion mechanism 42 mentioned later. In FIG. 1, the first arm 35 and the first traveling support frame 37 are located above the main axis X—X, while the second arm 36 and the second traveling support frame 38 are located below the main axis X—X. Further, the X-ray tube 14 and the image receiving device 15 vertically face each other with the main axis X—X between them, and the main plane is coincident with the drawing plane of FIG. 1. Thus, the X-rays advance substantially vertically upward through a path contained in the main plane, and are received by the image receiving device 15 after passing through the patient 12 lying on the table 13. In FIG. 1, an X-ray beam is represented by its center line $x_o$, and the intersection of the X-ray beam $x_o$ and the main axis X—X is indicated by a point a.

The first expansion tube member including the first arm 35 and the first traveling support frame 37 is fitted with the image receiving device 15, a first transfer means 22a (FIGS. 2 and 3) for transferring the image receiving device 15 along the main axis X—X, a first tilting means 22b (FIGS. 2, 3 and 4) for rotating the image receiving device 15 around the main point a within the main plane, and the conversion mechanism 42. The second expansion tube member including the second arm 36 and the second traveling support frame 38 is provided with the X-ray tube 14, a second transfer means 23a (FIGS. 8 and 9) for transferring the X-ray tube 14 along the main axis X—X, and a second tilting means 23b (FIGS. 7, 8 and 9) for rotating the X-ray tube 14 around the main point a within the main plane. In FIG. 1, two-dot chain lines 14a and 14b represent those positions of the X-ray tube 14 which are reached when the X-ray tube 14 is moved to the right and left and then tilted counterclockwise and clockwise, respectively, so that X-ray beams $x_a$ and $x_b$ passing through the main point a and each at an angle α to a vertical line are emitted from the X-ray tube 14, respectively. As for two-dot chain lines 15a and 15b, they represent those positions of the image received device 15 which are reached when the image receiving device 15 is moved to the right and left through a suitable distance and then tilted clockwise and counterclockwise, respectively, to receive X-ray from the X-ray tube 14.

Figure 2:
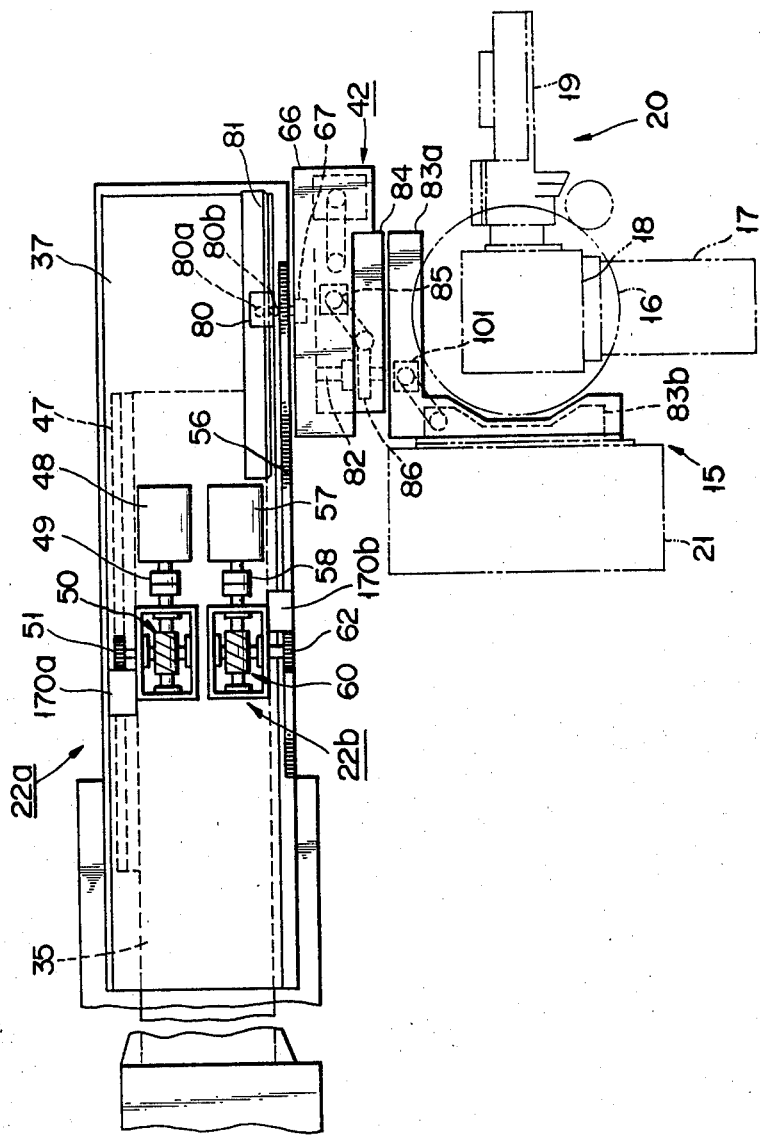
FIG. 2 is a plan view viewed from a ceiling side showing a mechanism for transferring an image receiving device of the apparatus of FIG. 1.
Figure 3:
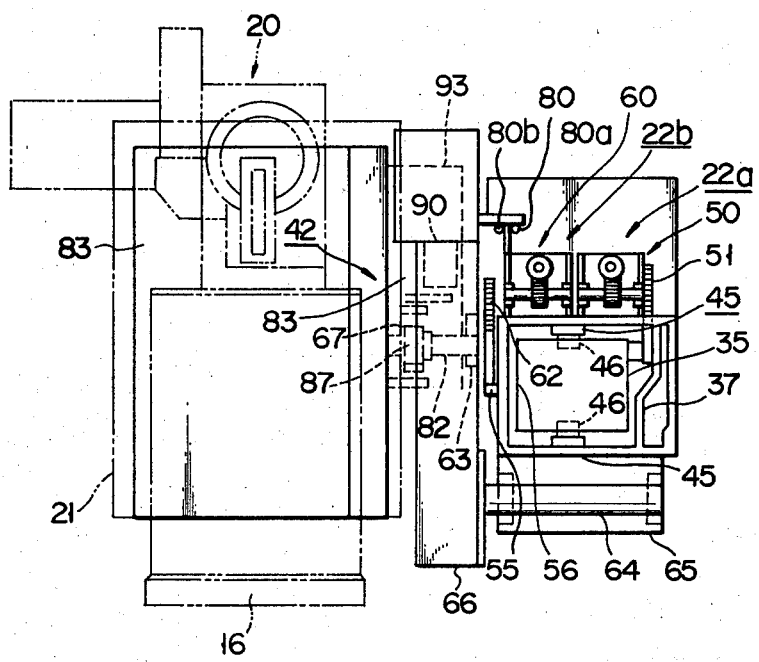
FIG. 3 is a right side view of the image receiving device of FIG. 1.
Figure 4:
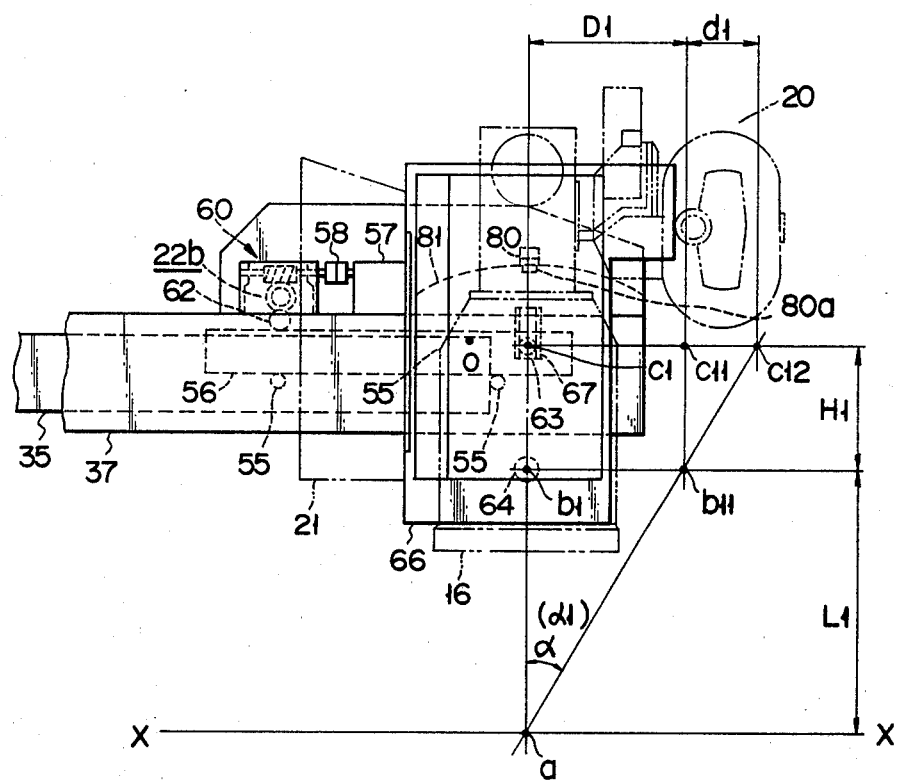
FIG. 4 is a front view showing such a state that the image receiving device of FIG. 1 is directed substantially vertically.

Referring now to FIGS. 2, 3 and 4, there will be described the first transfer means 22a, the first tilting means 22b, and the conversion mechanism 42. The first arm 35 and the first traveling support frame 37 are each in the form of a tube having a substantially rectangular cross section (FIG. 3). The first traveling support frame 37 is fitted on the first arm 35 so that the former can move to the right and left of FIG. 2, that is, along the main axis X—X, relatively to the latter. Such movement of the first traveling support frame 37 is achieved smoothly with the engagement between slide units 45 attached to the upper side and lower side of the first traveling support frame 37 and guide rails 46 provided in the first arm 35 along the main axis X—X. As shown in FIGS. 2 and 3, a fixed rack 47 is attached to the outer lateral face of the first arm 35, extending along the main axis X—X. Mounted on the upper side of the first traveling support frame 37 is a motor 48, whose rotation causes a spur gear 51 in mesh with the fixed rack 47 to rotate with the aid of a coupling 49 and a reduction gear mechanism 50 using a worm and a worm gear. Thus, the fixed rack 47 and hence the first traveling support frame 37 can be moved in either direction along the main axis X—X by rotating the motor 48.

Attached to the outer lateral face of the first traveling support frame 37, as shown in FIG. 4, is a movable rack 56 supported by a plurality of guide rollers 55 and capable of moving along the main axis X—X. A motor 57 mounted on the upper side of the first traveling support frame 37 drives a spur gear 62 in mesh with the movable rack 56 to rotate with the aid of a coupling 58 and a reduction gear mechanism 60 using a worm and a worm gear. As shown in FIG. 4, a pin 63 is attached to the tip end portion of the movable rack 56. Thus, the pin 63 can be moved in either direction along the main axis X—X by rotating the motor 57.

As shown in FIGS. 3 and 4, a bearing portion 65 supporting a shaft 64 protrudes from the lower end of the first traveling support frame 37. A tilting member 66 is rockably fitted on the tip end of the shaft 64, and a pair of guide rails 67 extending in the left and right directions of FIG. 4 along the vertical direction of FIG. 4 are attached to the surface of the tilting member 66, as shown in FIGS. 3 and 4. The pin 63 is interposed between the guide rails 67 to engage the same. Therefore, if the motor 57 is driven to move the pin 63 along the main axis X—X, then the tilting member 66 will rotate around the shaft 64. As seen from FIG. 2, the tilting member 66 is fitted with a guide member 80 having ball bearings 80a and 80b. The guide member 80 holds between the two bearings 80a and 80b thereof a guide member 81 extending along the main axis X—X on the first traveling support frame 37, and the tilting member 66 can smoothly rotate around the shaft 64 without flexure, guided by the guide member 81.

Figure 5:
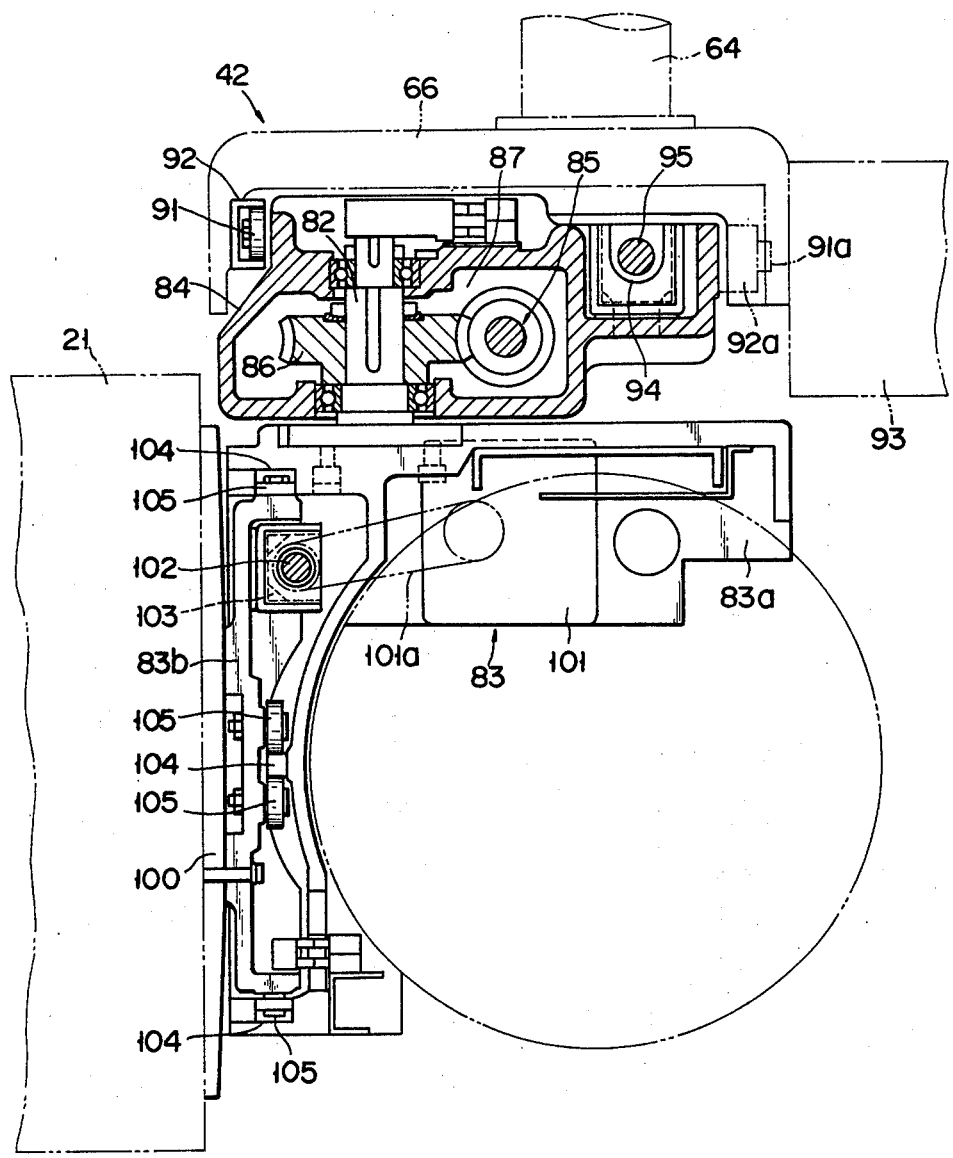
FIG. 5 is an enlarged sectional view of a conversion mechanism of the image receiving device of FIG. 2.
Figure 6:
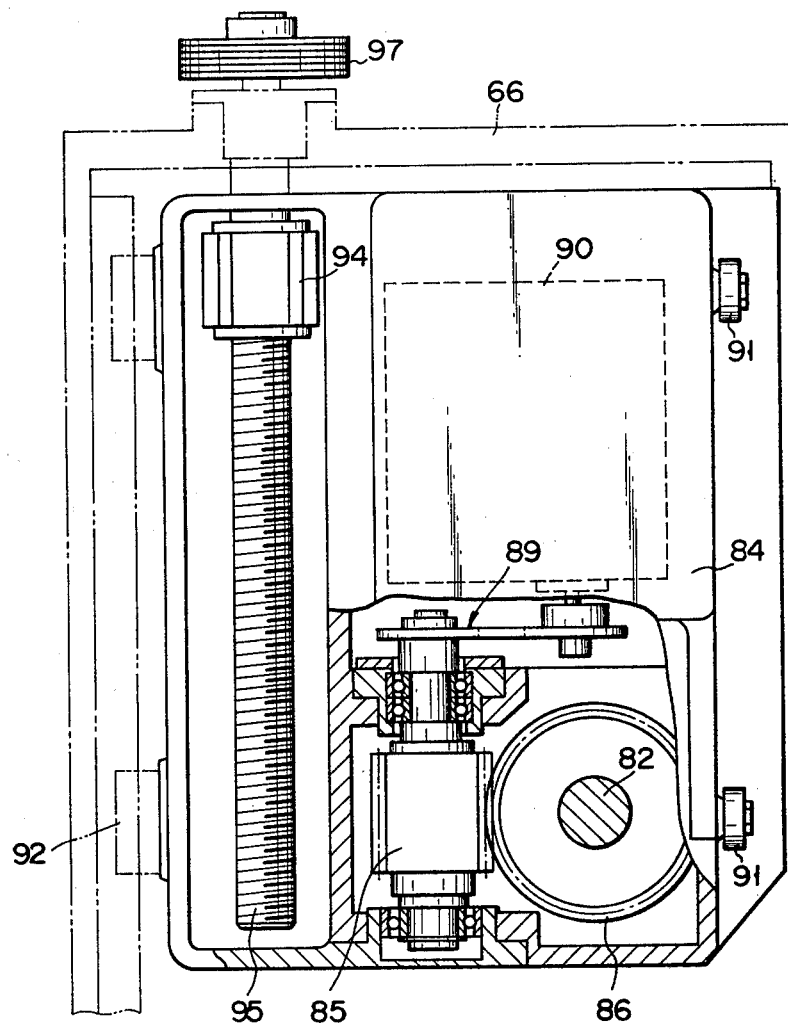
FIG. 6 is an enlarged sectional view of a gear box of FIG. 5.

FIG. 5 shows the image receiving device 15 attached to the tilting member 66. The image receiving device 15 includes the conversion mechanism 42 having a gear box 84 attached to the tilting member 66 and a metal fixture 83 coupled with the gear box 84, the cine unit 20 (only the I—I section 16 is shown in FIG. 5 for simplicity) attached to the conversion mechanism 42, and the FC unit 21. The gear box 84 includes a reduction gear mechanism 87 consisting of a worm 85 and a worm gear 86. When a motor (FIG. 3) rotates to drive the worm gear 86 with the aid of a suitable rotation transmission mechanism 89, a rotating shaft 82 fixedly mounted with the worm gear 86 and hence the fixture 83 are rotated. The gear box 84 can move relatively to the tilting member 66 in the direction normal to the drawing plane of FIG. 5, with the aid of rollers 91 attached to the gear box 84, guide rails 92 attached to the tilting member 66, guide rails 91a fixed to the tilting member 66 and slide units 92a fixed to the gear box 84 and engaged with the guide rails 91a. As a result, the I—I section 16, the cine unit 20 (FIG. 2) and the FC unit 21 can move vertically. The vertical movement of the gear box 84 is achieved by means of a nut member 94 attached to the gear box 84, a screw rod 95 (FIGS. 5 and 6) supported by the tilting member 66, and a drive mechanism 93 for rotating the screw rod 95. In FIG. 6, numeral 97 designates a pulley included in the drive mechanism 93. Thus, if the drive mechanism 93 is actuated, the screw rod 95 rotates to move verticaly the cine unit 20 and the FC unit 21, along with the gear box 84.

The fixture 83 is fitted with the cine unit 20 and the FC unit 21, both of which can rotate together with the rotating shaft 82 around the same so that the X-ray reception-side end portion of the desired one of the units may be directed at right angles to the drawing plane of FIG. 5. In FIG. 1, the I—I section 16 of the cine unit 20 faces downward, while the FC unit 21 looks to the left. In the state shown in FIG. 1, therefore, the X-ray beam $x_o$ projected substantially perpendicularly upward may be cinefilmed. FIG. 2 is a top view of the apparatus in such a state. In FIG. 2, the cine unit 20 and the FC unit 21 are represented by two-dot chain lines. The cine-filming may be switched to direct photographing using the FC unit by rotating the fixture 83 with the rotating shaft 82 through an angle of 90° so that the FC unit 21 may substantially reach the illustrated position of the I—I section 16. The rotated FC unit 21 is shifted a little along the course of the X-ray beam and along the direction normal to the course for positioning. The way of such positioning will later be described in detail. For the positioning, the fixture 83 is divided into two parts; a rotating portion 83a attached to the rotating shaft 82 and a sliding portion 83b attached to the rotating portion 83a at substantially right angles thereto and movable relatively to the rotating portion 83a. The cine unit 20 is attached to the rotating portion 83a, while the FC unit 21 is attached to the sliding portion 83b by means of a mounting plate 100. The rotating portion 83a is provided with a drive mechanism 101 including a pulley block 101a, and a screw rod 102 driven by the pulley block 101a. The sliding portion 83b is fitted with a nut member 103 mating with the screw rod 102, so that the sliding portion 83b and hence the FC unit 21 can be moved at right angles to the drawing plane of FIG. 5 by driving the drive mechanism 101. In this case, the sliding member 83b is moved smoothly by means of a guide portion 104 at the rotating portion 83a and a roller 105 attached to the sliding portion 83b and engaging the guide portion 104.

The first tube member including the first arm 35 and the first traveling support frame 37, the fixed rack 47, the motor 48, the reduction mechanism 50, the spur gear 51, the shaft 64, and the tilting member 66, as described above, constitute the first transfer means 22a, while the movable rack 56, the pin 63, and the guide rail 67 form the first tilting means 22b.

Further, the fixture 83, the drive mechanism 101, the pulley block 101a, the screw rod 102, the nut 103, the guide portion 104, and the roller 105 constitute the conversion mechanism 42.

Figure 7:
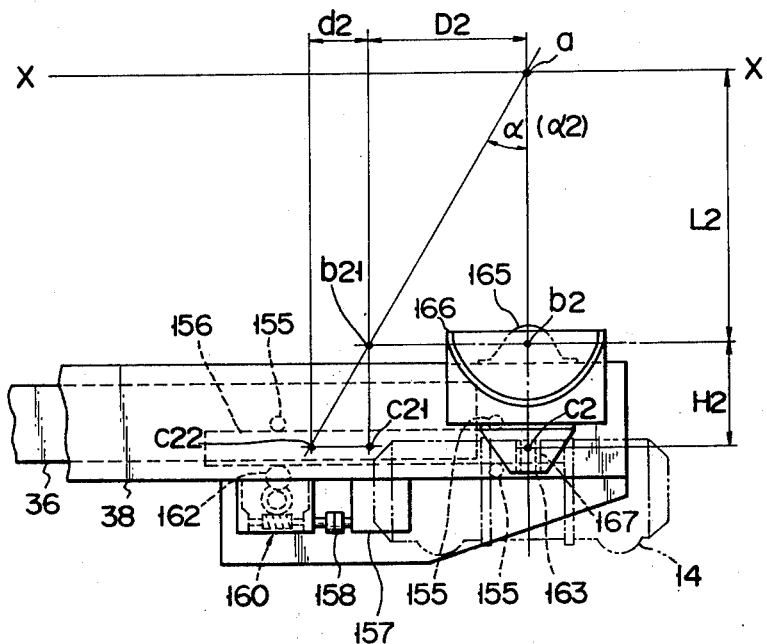
FIG. 7 shows geometrical relationships between associated members in such a state that the X-ray tube of FIG. 1 faces vertically upward and is going to be rotated clockwise through an angle α.
Figure 8:
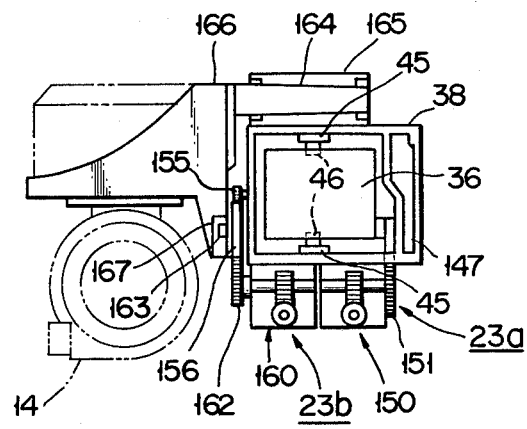
FIG. 8 is an enlarged right side view of the X-ray tube of FIG. 1.
Figure 9:
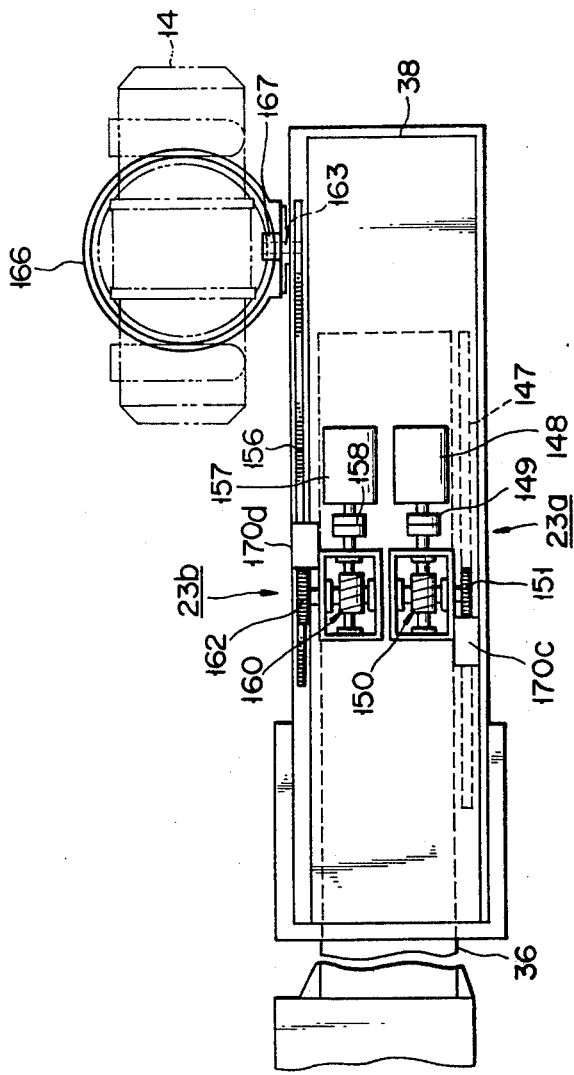
FIG. 9 is a bottom view of a mechanism viewed from a floor side for driving the X-ray tube of FIG. 7.

Referring now to FIGS. 7, 8 and 9, there will be described the second transfer means 23a and the second tilting means 23b. Since these means 23a and 23b have the same constructions and operate in the same manners as the first transfer means 22a and the first tilting means 22b do, respectively, so members included in the means 23a and 23b except the second arm 36 and the second traveling support frame 38 are denoted by numerals obtained by adding 100 to those numerals which designate their corresponding members in the means 22a and 22b. For example, members denoted by 50 and 150 have the same name and correspond to each other. Thus, the means 23a and 23b will be described only in brief. As shown in FIG. 9, a fixed rack 147 is attached to the second arm 36, while a movable rack 156 is attached to the second traveling support frame 38 so as to be movable along the main axis. The rotation of a motor 148 mounted on the second traveling support frame 38 is transmitted to a spur gear 151 through a reduction gear mechanism 150. When the spur gear 151 rotates, the second traveling support frame 38 moves along the main axis. Likewise, the rotation of a motor 157 mounted on the second traveling support frame 38 is transmitted through a reduction gear mechanism 160 to a spur gear 162 to drive the same. Accordingly, the movable rack 156 and hence a pin 163 attached to the tip end portion thereof move along the main axis. As shown in FIGS. 7 and 8, a tilting member 166 is pivotally supported on the second traveling support frame 38 by means of a shaft 164, and the pin 163 engages a guide rail 167 attached to the tilting member 166. Thus, when the movable rack 156 moves to the left, the tilting member 166 rotates in the clockwise direction of FIG. 7 around the shaft 164, and the X-ray tube 14 attached to the tilting member 166 comes to emit the X-rays to the upper right.

Figure 10:
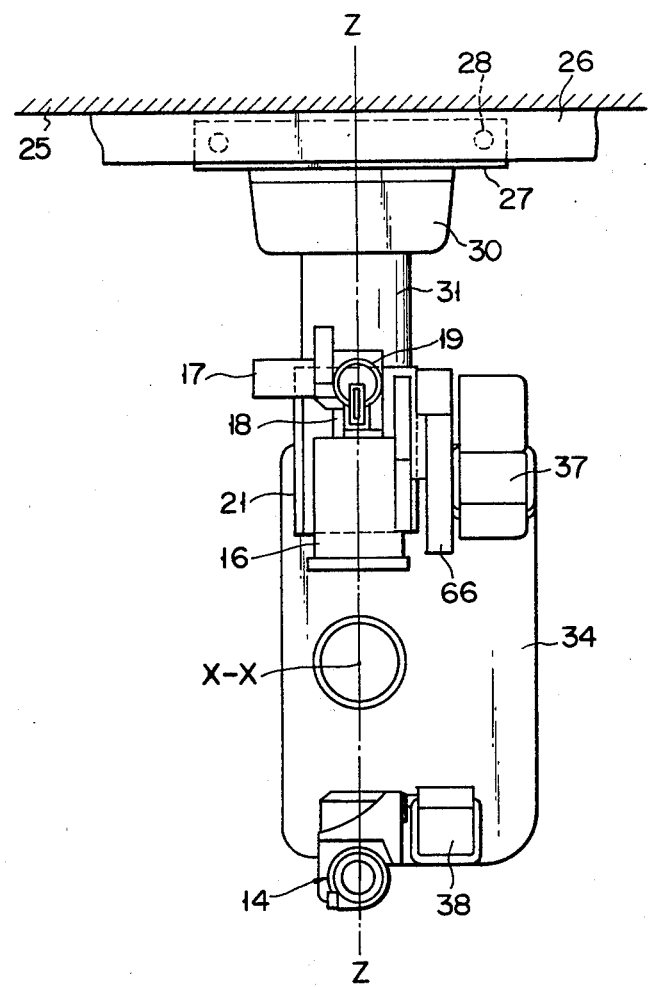
FIG. 10 is a right side view of the apparatus of FIG. 1.

FIG. 10 is a right side view of the apparatus shown in FIG. 1. The base 34 can rotate about the main axis X—X extending at substantially right angles to the plane of drawing. The X-ray tube 14 and the I—I section 16 are vertically opposed to each other with the main axis X—X between them so that the X-rays are projected substantially perpendicularly upward along the line Z—Z of FIG. 10.

Figure 11:
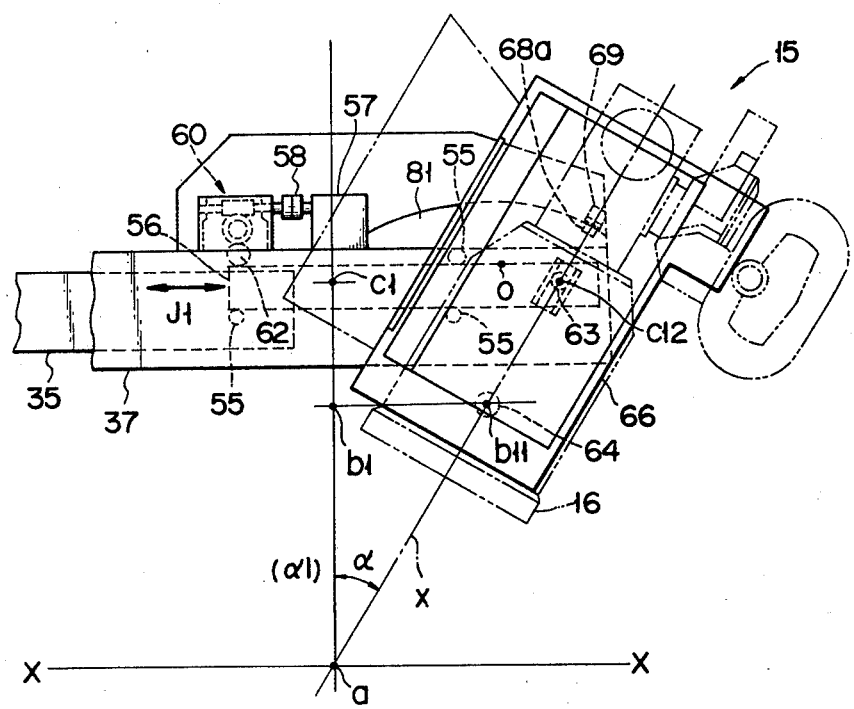
FIG. 11 shows such a state that a tilting member of FIG. 4 is titled at the angle α.

In FIG. 4, the I—I section 16 is directed downward so as to receive the X-rays radiated substantially vertically upward through the main point a, and the centers of the shaft 64 and the pin 63 are at points b1 and c1, respectively, on a vertical line passing through the main point a. If the motor 48 is driven while keeping the motor 57 stopped, the spur gear 51 rotates to allow the I—I section 16, along with the first traveling support frame 37, to move along the main axis while facing vertically downward. Accompanying the I—I section 16, the cinecamera 17, the TV camera 18, and the optical system 18 also move. In the below description, the I—I section 16 is mentioned as a representative of those devices 17, 19 and 18. In FIG. 4, if the I—I section 16 is moved to the right through a distance D1 to cause the shaft 64 to reach a point b11, the pin 63 reaches a point c11 at the distance D1 from the point c1. Thereafter, if the I—I section 16 is rotated clockwise through an angle $\alpha$, it turns right to the main point a. The angle $\alpha$ is equivalent to an angle between a straight line connecting the points a and b1 and a straight line connecting the points a and b11. In changing the direction of the I—I section 16 in the aforesaid manner, the motor 57 is driven to move the movable rack 56 and hence the pin 63 to the right through a distance d1 or (D1/L1)H1 where L1 is the distance between the points a and b1 of FIG. 1, and H1 is the distance between the points b1 and c1. Then, the tilting member 66 tilts clockwise at the angle $\alpha$ to a vertical line, as shown in FIG. 11, so that the I—I section 16 can correctly receive an X-ray beam x which is radiated along a straight line passing through the points a and b11. This can be done because a triangle with vertices b11, c11 and c12 is similar to a triangle with vertices a, b1 and b11 since we have d1=(D1/L1)H$_1$ and hence (d1/H1)=(D1/L1), and because a straight line connecting the points c12 and b11 passes through the main point a. In FIG. 11, the image receiving device 15 is drawn with two-dot chain line so that it may look distinctly outlined against the first traveling support frame 37 and the tilting member 66.

Figure 12:
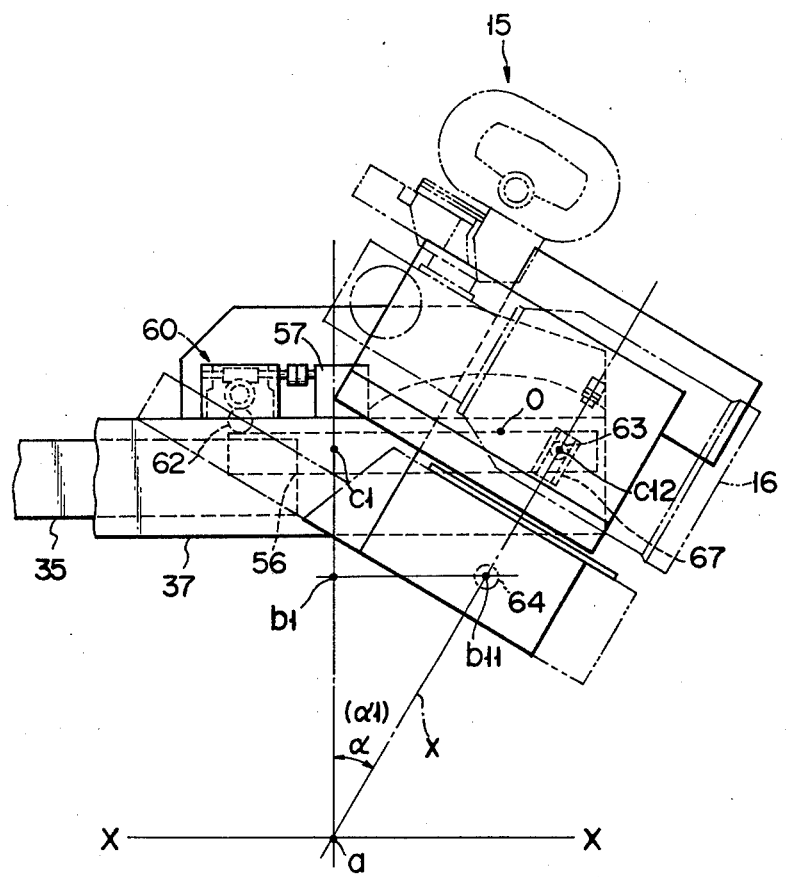
FIG. 12 shows such a state that the image receiving device in the state of FIG. 11 is rotated counterclockwise to allow X-ray photographing by an FC unit.

In FIG. 11, the image receiving device 15 stands ready for cine-filming with the I—I section 16 receiving the X-ray beam x radiated along the line passing through the points a and b11. FIG. 12 shows such a state that the FC unit 21 is allowed to photography by rotating the image receiving device 15 in the position shown in FIG. 11 counterclockwise at approximately 90° to the line of the X-ray beam x around the rotating shaft 82. The FC unit 21 directed along the X-ray beam x by the rotation of the image receiving device 15 is so positioned that X-rays may normally be applied to the central portion of a photographic film to enable photographing with the same magnification as that for the cine-filming. This point will later be explained.

Figure 13:
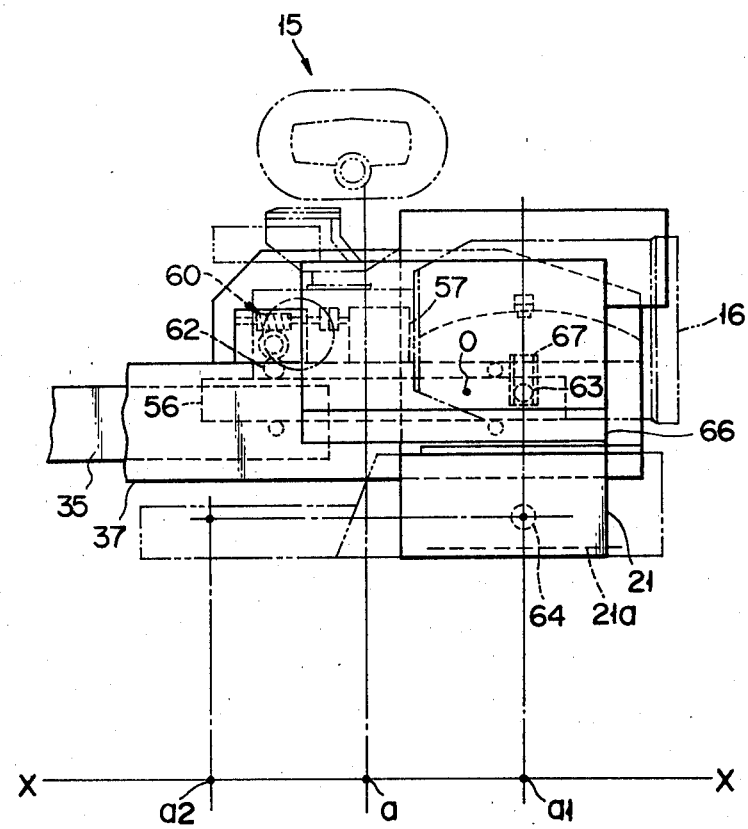
FIG. 13 shows such a state that the FC unit included in the image receiving device of FIG. 1 faces vertically downward with the frame being fully extended.

FIG. 13 shows such a state that the FC unit 21 is allowed to receive the X-rays projected vertically upward by rotating the image receiving device 15 in the position of FIG. 4 counterclockwise at approximately 90°. Also in this case, the first traveling support frame 37 can be moved horizontally by driving the motor 48 of FIG. 2 so that the FC unit 21 may receive those X-ray beams which are radiated upward through various points, such as points a, a1 and a2.

FIG. 7 shows such an arrangement that the X-ray tube 14 projects X-rays vertically upward on the I—I section 16 in the position of FIG. 4 through the main point a. As seen from FIG. 7, the shaft 164 attached to the second traveling support frame 38 and supporting the tilting member 166 and the pin 163 at the right end portion of the movable rack 156 are substantially plumb under the main point a. The main point a of FIG. 7 is identical with the main point a of FIG. 4. The horizontal or longitudinal position of the shaft 164 may be set as required by rotating the motor 148 of FIG. 9 to move the second traveling support frame 38 horizontally. The pin 163 may be located in a desired position by driving the motor 157 of FIG. 9 to move the movable rack 156 horizontally as compared with the second traveling support frame 38. Thus, the X-ray tube 14 can radiate the X-rays at a desired angle to a vertical line. In photographing the patient with use of the X-rays from the X-ray tube 14 in the position of FIG. 7, with the I—I section 16 in the position of FIG. 4, it is necessary only that the first and second traveling support frames 37 and 38 be expanded or contracted by means of the motors 48 and 148 so that an X-ray beam passed through the patient may come substantially into the center of the I—I section 16.

Figure 14:
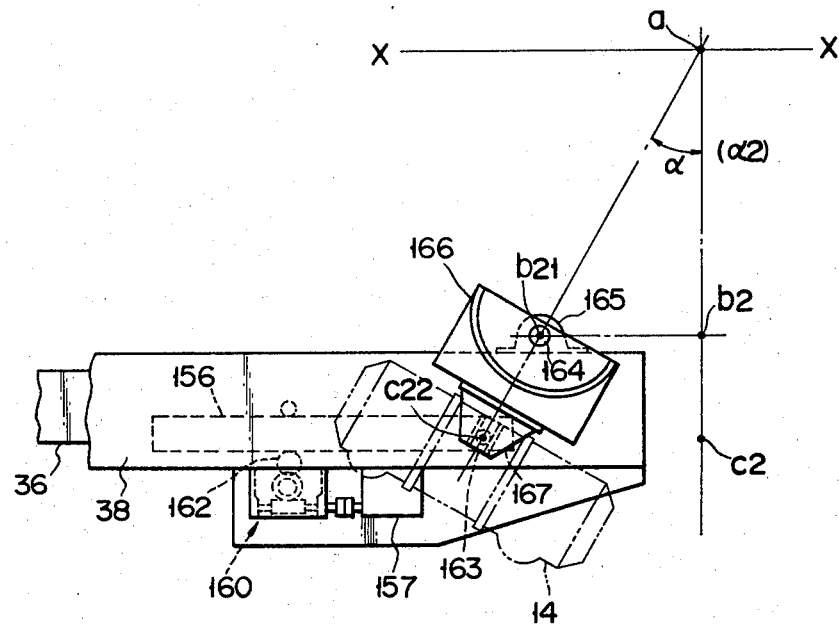
FIG. 14 shows such a state that the X-ray tube of FIG. 1 is rotated clockwise through the angle α.

Then, if the image receiving device 15 is tilted as shown in FIG. 11 to receive the X-ray beam x passing through the main point a, it is necessary that the X-ray tube 14 in the position of FIG. 7 be adjusted in position and direction so that the course of the radiated X-ray beam is coincident with that of the X-ray beam x of FIG. 11. To attain this, the shaft 164 need be transferred from a point b2 to a point b21 of FIG. 7, and the pin 163 need be transferred from a point c2 through a point c21 to a point c22. This can be achieved by moving the second traveling support frame 38 to the left through a distance D2 in FIG. 7 and the movable rack 156 to the left through a distance d2 as compared with the second traveling support frame 38. If we have only $(D2/L2)=(d2/H2)=\tan \alpha$, the points b21, c22 and a will be on one and the same straight line, and the extension of this straight line will be coincident with the course of the X-ray beam x of FIG. 11. Here L2 is the distance between the main point a and the center b2 of the shaft 164, and H2 is the distance between the center b2 and the center c2 of the pin 163. FIG. 14 shows the second traveling support frame 38 and the movable rack 156 in positions reached after they are moved in the aforesaid manner. As seen from FIG. 14, the X-ray beam from the X-ray tube 14 is received as the X-ray beam x of FIG. 11 by the I—I section 16 after passing through the main point a.

Figure 15:
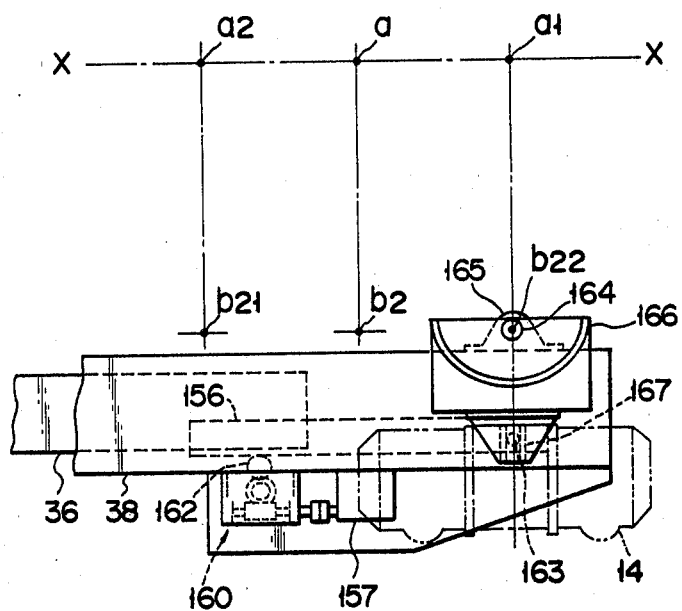
FIG. 15 shows such a state that the X-ray tube of FIG. 1 faces vertically upward with the frame being fully extended.

FIG. 15 shows three positions of the X-ray tube 14 which correspond to the three main points a1, a and a2 of the FC unit 21 shown in FIG. 13. In this case, X-rays emitted from the X-ray tube 14 advance substantially vertically, so that the tilting member 166 need only be transferred horizontally from the position of FIG. 7 to be located substantially plumb under the FC unit 21 without tilting. It is to be understood that the expansion or contraction of the second traveling support frame 38 is utilized for such transfer. The points a, a1 and a2 of FIG. 15 are identical with the points a, a1 and a2 of FIG. 13, respectively.

Figures 16A, 16B, 16C, 16D:
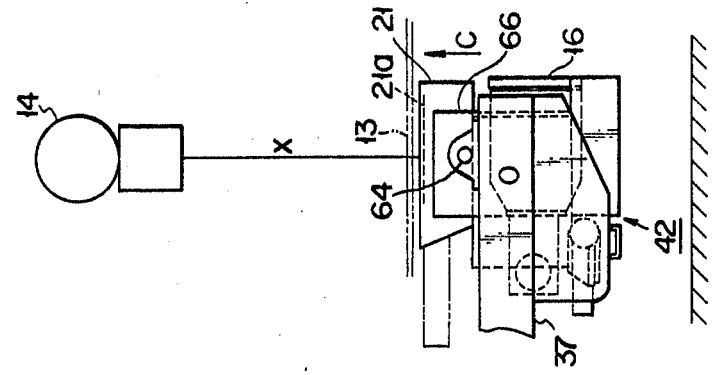
FIGS. 16A, 16B, 16C and 16D show how a conversion mechanism operates when switching the apparatus from cine-filming to photographing by means of the FC unit.

There will now be described the operation of the conversion mechanism 42 whose construction is described with reference to FIG. 5. FIGS. 16A to 16D show how the image receiving device 15 shifts its direction and position when the base 34 of FIG. 1 rotates through approximately 180° around the main axis X—X so that the first traveling support frame 37 is located under the table 13 and that the X-ray beam x is radiated from the X-ray tube 14 on the upper side. FIG. 16A shows such a state that the I—I section 16 of the cine unit 20 is located right under the table 13, facing upward to stand ready for fluoroscopy-filming, and the FC unit 21 is in a nonoperating position, looking to the left. A broken line at the left end portion of the FC unit 21 represents the position of a film 21a for X-ray image photographing in the FC unit 21. FIG. 16B shows the state of things after the motor 90 of FIG. 6 is driven to rotate the fixture 83 in the clockwise direction indicated by an arrow A through approximately 90° around the axis O of the rotating shaft 82.

Although the X-ray receiving end portion of the FC unit 21 should be located as close to the patient of the table 13 as possible, the FC unit 21 is temporarily evacuated to a position off the suitable position for X-ray photographing during the clockwise rotation thereof lest the upper end edge of the FC unit 21, having the larger frontage than that of the I—I section 16, should be caused to strike against the table 13 by such rotation. Therefore, even though the FC unit 21 is caused substantially to face the incident X-ray beam by the clockwise rotation, it is still to be desired that the center of the film 21a should be aligned with the X-ray beam, or that the magnification of the X-ray image changed by the aforesaid evacuation should be restored to a proper value.

In the state of FIG. 16B, the center of the film 21a is shifted to the left from its normal position for photographing due to the evacuation of the FC unit 21, and an oversized gap is created between the table 13 and the FC unit 21 caused to face vertically upwardy by the clockwise rotation.

In FIGS. 16A and 16B, a circular arc with a radius R described around the axis O in the vicinity of the table 13 indicates the limit of projection of any member within which members will be kept from interfering with one another at the time of the aforesaid clockwise rotation.

The axis O is so positioned that the torques on the rotating shaft 82 (FIG. 5) caused by the cine unit 20 and the FC unit 21 may cancel each other over the widest possible range of rotation.

The FC unit 21 in the position shown in FIG. 16B is transferred to the right or in the direction indicated by an arrow B of FIG. 16C so that the X-ray beam x may be applied to the center of the film 21a. The transfer of the FC unit 21 in the direction B is achieved by operating the drive mechanism 101 of FIG. 5 to turn the screw rod 102. FIG. 16C shows the position of the FC unit 21 reached after such transfer. As seen from FIG. 16C, however, the FC unit 21 is kept wide apart from the table 13, so that the magnification of an image provided by the FC unit 21 would be too high. Accordingly, the drive mechanism 93 of FIG. 5 is driven to turn the screw rod 95 so as to bring the FC unit 21 close to the table 13. As a result, the gear box 84 of FIG. 5, the fixture 83 coupled thereto, the cine unit 20, and the FC unit 21 all move in the direction indicated by an arrow C of FIG. 16D to the position nearer to the table 13, as shown in FIG. 16D, thereby adjusting the magnification of the image to a desired value. The photographing by the FC unit 21 may be switched to the filming by the cine unit 20 by inversely following the aforementioned processes.

Figure 17:
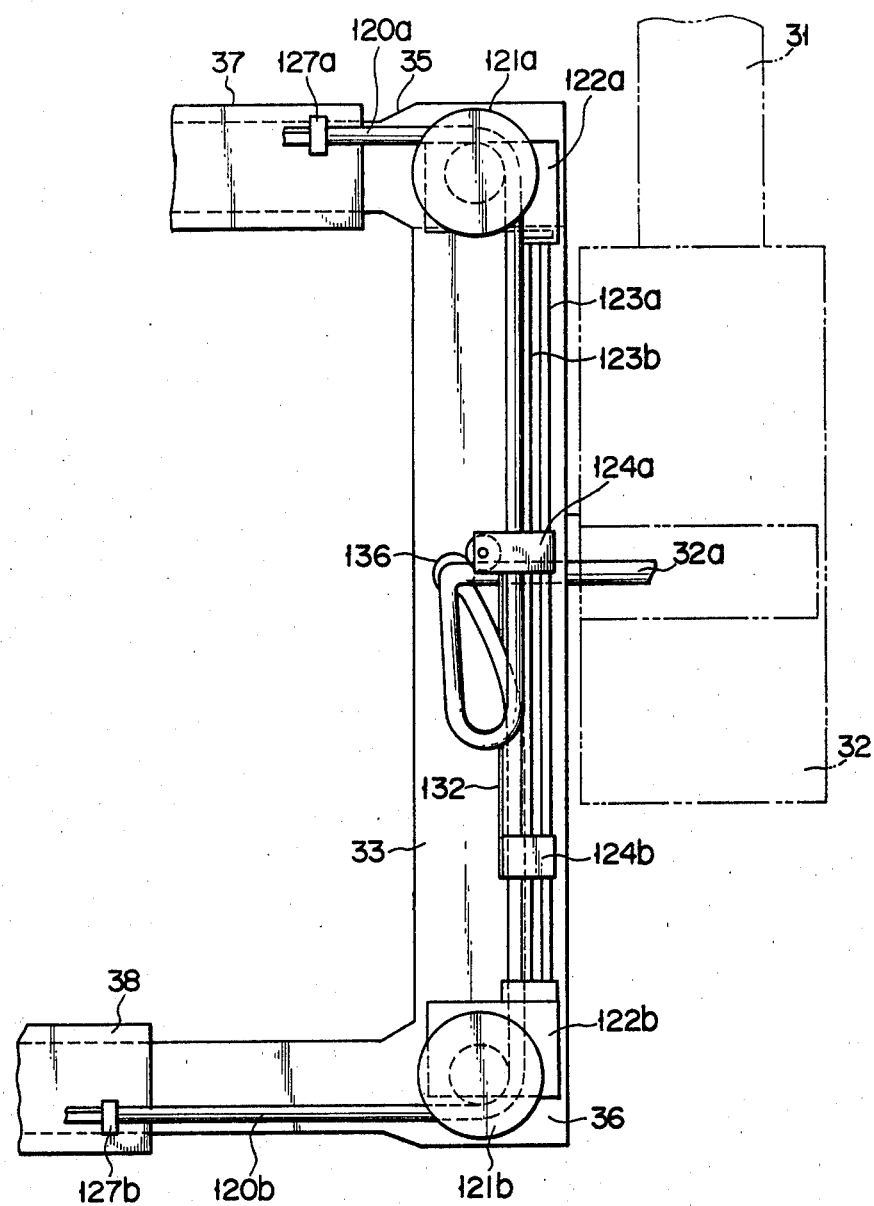
FIG. 17 is a rear side view of FIG. 1.
Figure 18:
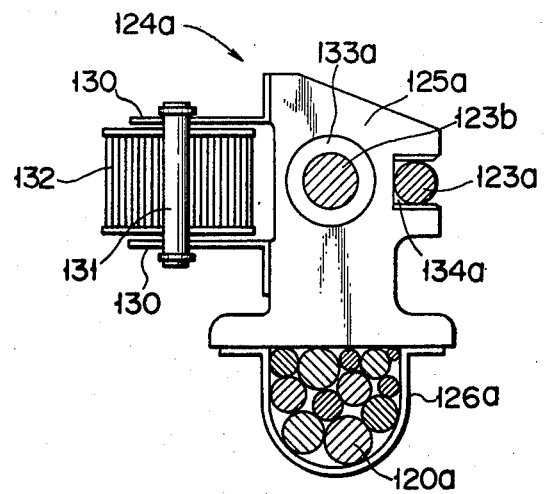
FIGS. 18 and 19 are enlarged sectional top views of two slide members of different types, respectively, used in the device of FIG. 17.
Figure 19:
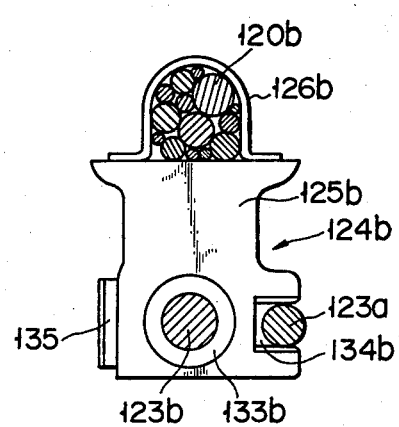

FIG. 17 is an enlarged view showing the rotating body 33, the second rotation mechanism 32, part of the expansion mechanism 31, the first and second arms 35 and 36, and parts of the first and second traveling support frames 37 and 38 shown in FIG. 1. As shown in FIG. 1, the first traveling support frame 37 is fitted with the image receiving device 15, the first transfer means 22a, and the first tilting means 22b. A cable 120a connected with the device 15 and the means 22a and 22b is drawn out of the apparatus through the first traveling support frame 37. The second traveling support frame 38 is provided with a cable 120b which is connected with the X-ray tube 14, the second transfer means 23a, and the second tilting means 23b, the tip end of the cable 120b being drawn out of the apparatus. The cables 120a and 120b are each formed of a bundle of many insulated wires. Pulleys 121a and 121b are attached to those portions of the rotating body 33 from which the first and second arms 35 and 36 project, respectively. Moreover, frames 122a and 122b are attached to the rotating body 33, while guide bars 123a and 123b are vertically disposed between the frames 122a and 122b. The guide bars 123a and 123b are fitted with slide members 124a and 124b as shown in detail in the top views of FIGS. 18 and 19, respectively. The slide member 124a of FIG. 18 has a slide block 125a and a clamp 126a. The clamp 126a is intended to fasten tight to the slide block 125a the cable 120a which extends downward around the pulley 121a after it is attached to the first traveling support frame 37 by a fixing means 127a, as shown in FIG. 17. The slide block 125a is fitted with two mounting plates 130 between which a shaft 131 is fixed. The inner end portion of a constant-load spiral spring 132 is attached to the shaft 131. For a clear understanding of the construction, the spiral spring 132 is shown in section. The slide block 125a is provided with a slide unit 133a having a guide hole through which the guide bar 123b is passed, and a guide groove 134a engaging the guide bar 123a. The slide member 124b of FIG. 19 has a slide block 125b and a clamp 126b. The clamp 126b is intended to fix to the slide block 125b the cable 120b which extends upward around the pulley 121b after it is attached to the second traveling support frame 38 by a fixing means 127b, as shown in FIG. 17. The slide block 125b is provided with a slide unit 133b having a guide hole through which the guide bar 123a is passed, a guide groove 134b engaging the guide bar 123b, and a support portion 135 to which the outer end of the spiral spring 132 is fixed. As shown in FIG. 17, the slide members 124a and 124b both engage the guide bars 123a and 123b so as to be able to move up and down along the guide bars 123a and 123b. The spiral spring 132 attached to the slide member 124a extends downward to have its outer end fixed to the support portion 135 of the slide member 124b. Thus, the two slide members 124a and 124b are always urged to approach each other along the guide bars 123a and 123b. The cables 120a and 120b clamped by the slide members 124a and 124b are drawn into the rotating body 33 through a hole therein, each with a portion of a suitable length left slackened, and are then passed through a hole 32a (FIG. 17) in the second rotation mechanism 32 to come out therefrom. The cables 120a and 120b are fixed to the rotating body 33 by a suitable holding means 136 at the opening portion of the hole in the rotating body 33.

While using the X-ray photography apparatus of FIG. 1, the first and second traveling support frames 37 and 38 are moved relatively to the first and second arms 35 and 36 and hence to the rotating body 33 along the main axis as required. Accompanying such movement of the support frames 37 and 38, the slackened portions of the cables 120a and 120b between the holding means 136 and the fixing means 127a and 127b of the first and second traveling support frames 37 and 38 are shortened or lengthened. Without a contermeasure, therefore, the cables 120a and 120b would take irregular shapes, possibly harshly touching each other or other members or slipping off the pulleys 121a and 121b. To avoid this, there is provided a cable smoothing device 137 including the pulleys 121a and 121b, the slide members 124a and 124b, and the guide bars 123a and 123b. If the first traveling support frame 37 moves to the right of FIG. 17, then the cable 120a will move downward, accompanying the slide member 124a which is continually pulled downward with a substantially constant force by the agency of the constant-load spiral spring 132. Thus, the cable 120a will neither be slackened between the fixing means 127a and the slide member 124a, nor slip off the pulley 121a. Between the slide member 124a and the holding means 136, on the other hand, the cable 120a will have a slackened portion corresponding to the rightward movement of the first traveling support frame 37. This slackened portion will not, however, exert any influence on the operation of the apparatus. If the first traveling support frame 37 moves to the left, the slide member 124a rises to shorten the slackened portion. Also in this case, the cable 120a will never be slackened between the fixing means 127a of the first traveling support frame 37 and the clamp 126a of the slide member 124a.

The slide member 124b is always pulled upward with a substantially constant force by the agency of the spiral spring 132. If the second traveling support frame 38 moves to the left or right, therefore, the slackened portion of the cable 120b between the clamp 126b of the slide member 124b and the holding means 136 of the rotating body 33 will be extended or shortened. The cable 120b will not, however, be slackened between the fixing means 127b of the second traveling support frame 38 and the clamp 126b. Thus, the cable 120b will never slip off the pulley 121b. Any change in length of the slackened portion between the holding means 136 and the clamp 126b will not have an influence on the operation of the apparatus. When X-ray is projected to the patient at various angles within the main plane, the first and second traveling support frames 37 and 38 are usually extended over different lengths from the first and second arms 35 and 36, respectively. In this case, the greater the extension of each traveling support frame, the shorter the slackened portion of its corresponding cable will be. Even though the cable has a relatively long slackened portion, it will never slip off its corresponding pulley since that portion of the cable on the pulley is strained. Further, the operation of the apparatus will not be influenced by the size of the slackened portions.

Figure 20:
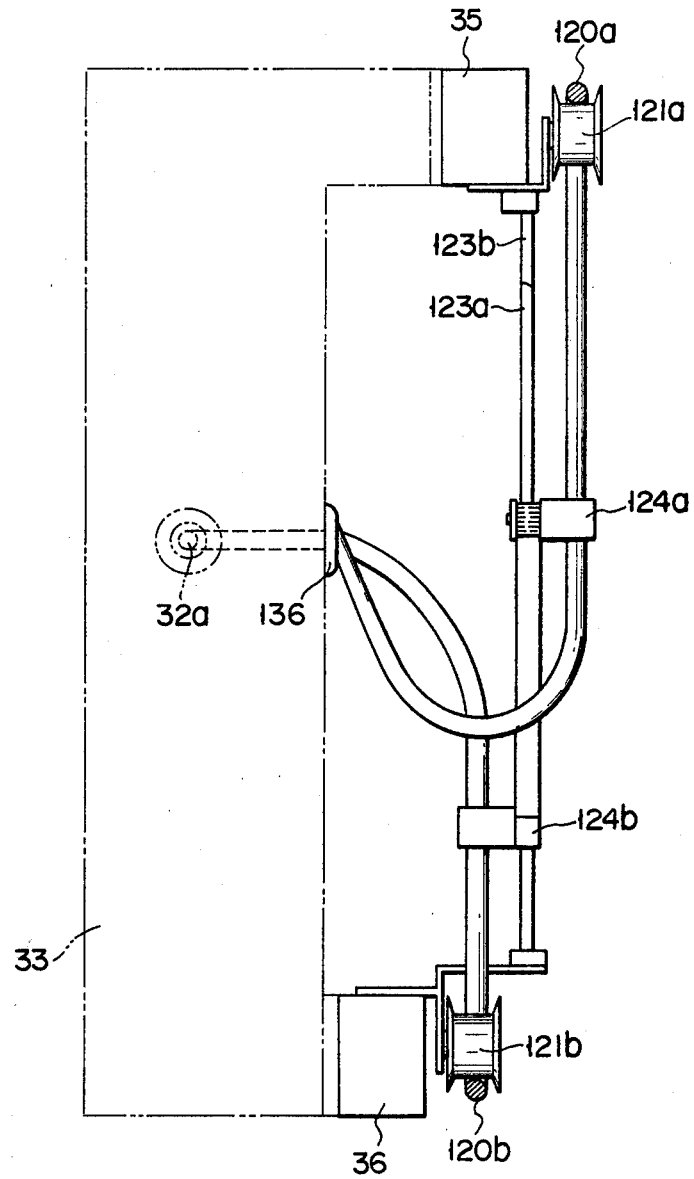
FIG. 20 is a left side view of the device of FIG. 17.

FIG. 20 is a side view of the principal part of the cable smoothing device 137 as viewed from the right of FIG. 17. The positional relationships between the several members shown in FIG. 17 will be more apparent from FIG. 20.

In the above-mentioned X-ray photography apparatus, the image receiving device 15 can be moved along the main axis to a desired position, and can also be turned in a desired direction within the main plane by driving the motors 48 and 57 shown in FIG. 2. Further, the X-ray tube 14 can be moved along the main axis to a desired position, and can also be turned in a desired direction within the main plane, independently of the image receiving device 15, by driving the motors 148 and 157 shown in FIG. 9. By driving the second rotation mechanism 32 of FIG. 1, moreover, the X-ray tube 14 and the image receiving device 15 can be rotated around the main axis X—X. Thus, the aforementioned first to fifth photographing methods can be all executed by means of the single apparatus. Furthermore, the first and second traveling support frames 37 and 38 can be moved over a distance or length exceeding the half length of the stature of any patient, so that every part of the upper half and the lower half of a patient can be X-rayed, respectively, from any desired direction without moving the patient, and a film or other X-ray receiving surface can be turned in a desired direction of X-ray photographing.

Figure 21A:
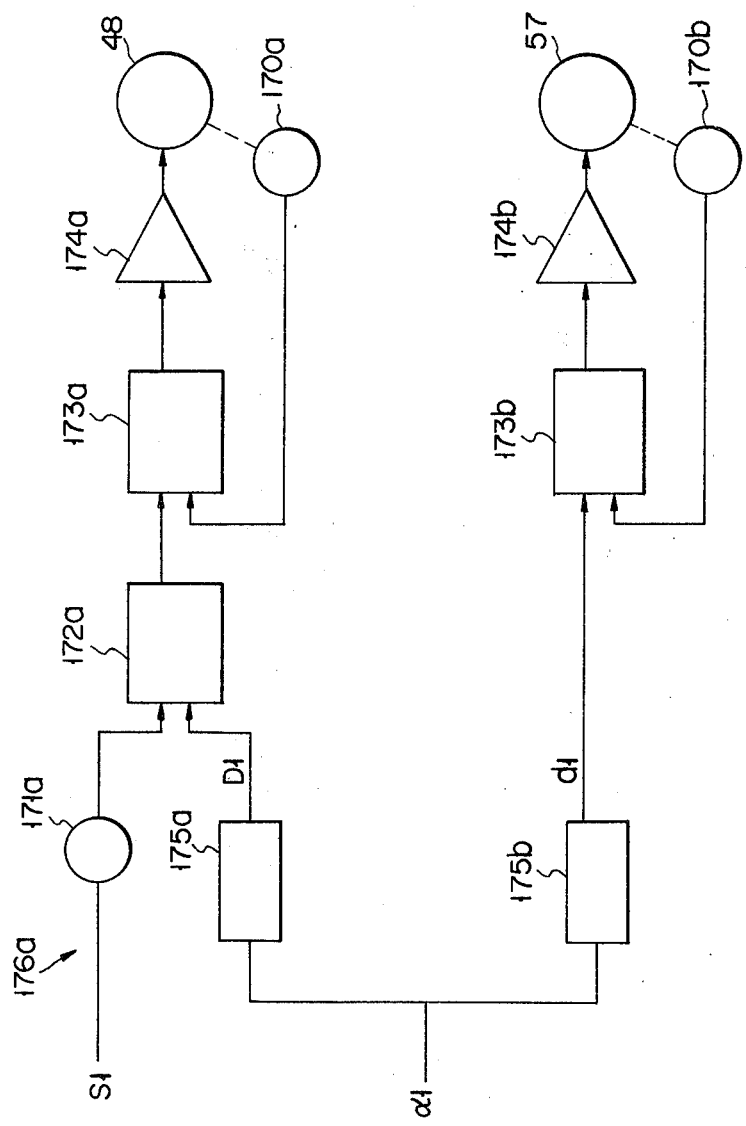
FIG. 21A is a block diagram of a circuit for controlling the movement and tilting motion of the image receiving device of FIG. 2.

FIG. 21A shows an example of a control circuit used for transferring the I—I section 16 from a predetermined reference point (not shown) to the right of FIG. 11 while keeping it facing downward, and then turning it in a direction at an angle $\alpha 1$ to a vertical line passing through the main point a determined by the transfer. The angle $\alpha 1$ is used for discrimination from an angle $\alpha 2$ to define the X-ray radiating direction as mentioned later. In the description to follow, therefore, $\alpha 1$ and $\alpha 2$ are used in place of $\alpha$ for the tilts of the image receiving device 15 and the X-ray tube 14, respectively. In the drawings, $\alpha 1$ and $\alpha 2$ are parenthesized beside $\alpha$. In this control circuit, the moved distance of the first traveling support frame 37 depends on the angle of rotation of the motor 48 of FIG. 2, so that a feedback potentiometer 170a (FIG. 2) to rotate on the basis of the rotation of the spur gear 51 is used for detecting the moved distance. In FIG. 21A, a broken line connecting the motor 48 and the potentiometer 170a indicates the mechanical coupling between them. In FIG. 21A, numeral 171a designates a command potentiometer which delivers an output voltage equivalent to the distance from the predetermined reference point to be covered by the first traveling support frame 37. Further, numerals 175a and 175b designate tilt command generators which deliver voltages equivalent to the distance d1 or L1 tan $\alpha 1$ and the distance d1 or H1 tan $\alpha 1$, respectively, of FIG. 4 when the angle $\alpha$ is set. An adder 172a adds up the output voltages of the potentiometer 171a and the generator 175a, and delivers an output voltage equivalent to $S_1 + D1$. A comparator 173a delivers the difference between the outputs of the adder 172a and the feedback potentiometer 170a. This difference is amplified by an amplifier 174a to drive the motor 48. This drive is continued until the output of the comparator 173a is reduced to zero. When the motor 48 stops, the first traveling support frame 37 is so positioned that the shaft 64 is at the point b11 of FIG. 4.

While the first traveling support frame 37 is moved to such position, the movable rack 56, which is attached to the support frame 37 so as to be movable along the main axis, is so moved as to tilt the I—I section 16 at the angle $\alpha 1$. Since the moved distance of the movable rack 56 relative to the first traveling support frame 37 is proportional to the rotation angle of the motor 57 of FIG. 2, it is detected by using a feedback potentiometer 170b which rotates on the basis of the rotation of the spur gear 62 in mesh with the movable rack 56. Numerals 173b and 174b designate a comparator and an amplifier which correspond to the comparator 173a and the amplifier 174a, respectively. By the use of the control circuit 176a of FIG. 21A, therefore, the I—I section 16 can be turned in a direction at the angle $\alpha 1$ to a vertical line and along a straight line passing through the main point at a distance S1 from the reference point. The relationship between the vertical line, the distances D1 and d1, and the angle $\alpha 1$ are as illustrated in FIG. 4.

Figure 21B:
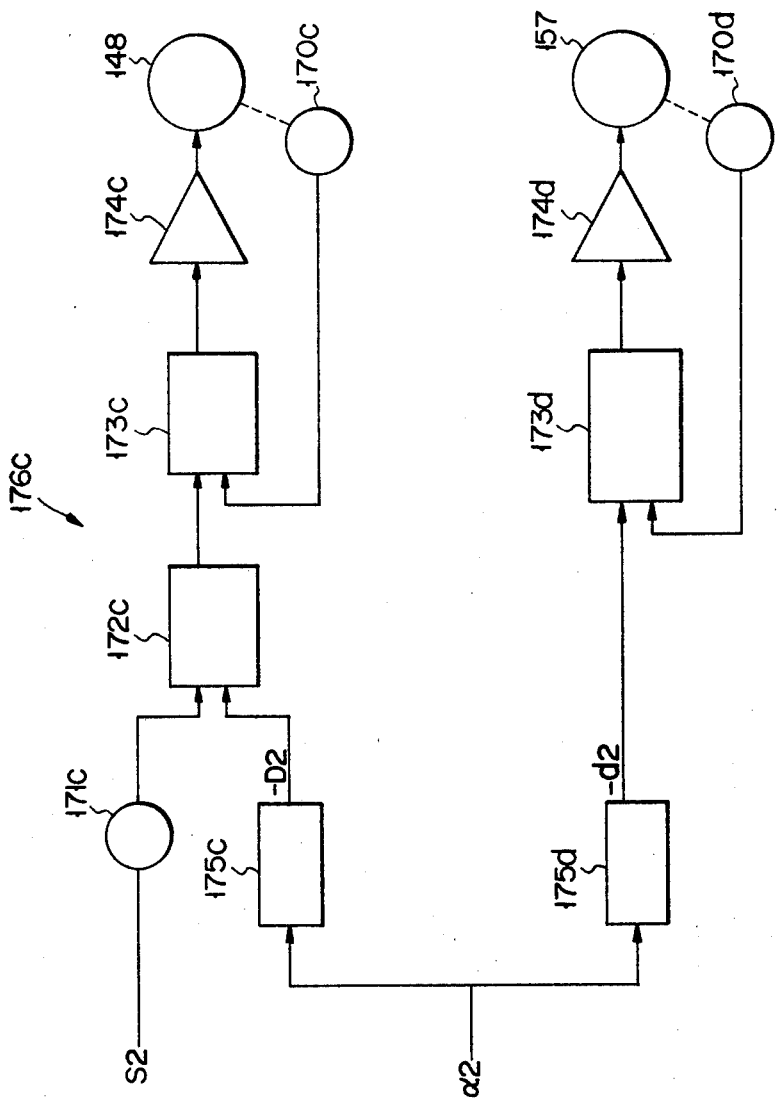
FIG. 21B is a block diagram of a circuit for controlling the movement and tilting motion of the X-ray tube of FIG. 9.

FIG. 21B shows a control circuit 176b used, independently of the control circuit 176a described in connection with FIG. 21A, for turning the X-ray tube 14 in a direction at the angle $\alpha 2$ to the vertical line passing through the main point (point a of FIG. 7) at a distance S2 from a suitable reference point. In FIG. 14, the angle $\alpha 2$ is expressed together with $\alpha$ so that it may be distinguished from the tilt angle $\alpha 1$ for the case of the control circuit 176a. Being of the same type as the control circuit of FIG. 21A, the control circuit of FIG. 21B will be described only briefly. In FIG. 21B, numerals 170c and 170d designate feedback potentiometers to rotate on the basis of the rotation of the spur gears 151 and 162 of FIG. 9, respectively. The potentiometer 170c delivers an output voltage equivalent to the moved distance of the second traveling support frame 38, while the potentiometer 170d delivers an output voltage equivalent to the moved distance of the movable rack 156 relative to the second traveling support frame 38. Numeral 171c denotes a command potentiometer to produce a voltage for moving the second traveling support frame 38 through the desired distance S2 from the predetermined reference position (not shown), and numerals 175c and 175d designate tilt command generators which produce output voltages equivalent to the length $-D2$ or $-L2$ tan $\alpha 2$ and the length $-d2$ or $-H2$ tan $\alpha 2$, respectively, of FIG. 7 when the angle $\alpha 2$ is given. In FIG. 21B, moreover, numeral 172c designates an adder; 173c and 173d comparators and 174c and 174d amplifiers.

If the command potentiometer 171c is set to S2 and if the tilt command generators 175c and 175d are set $\alpha 2$, the second traveling support frame 38 moves to the left so that the shaft 164 may be located in a position at the distance D2 from the point b2 of FIG. 7, and at the same time the movable rack 156 moves to the left through d2. As a result, the X-ray tube 14 takes the position and direction corresponding to S2 and $\alpha 2$.

By setting suitable values for S1, α1, S2 and α2 in the control circuits 176a and 176c, as described above, it is possible to determine as desired the position and X-ray radiating direction of the X-ray tube 14, the position of the image receiving device 15, and the X-ray receiving direction of the device 15 or the direction normal to an X-ray receiving fluorescent screen and film in the I—I section 16 and the FC unit 21. Accordingly, any of the aforementioned first to fifth photographing methods can be executed by using the function of the second rotation mechanism 32 of FIG. 1 to rotate the first and second traveling support frames 37 and 38 around the main axis X—X, as well as the above-mentioned functions.

In the X-ray photography using the control circuits 176a and 176c, correlative values are chosen for the parameters S1, S2, α1 and α2 for the circuits, depending on the photographing method used. For example, if $\alpha1=\alpha2$ $(=\alpha)$ and $S1=S2$ $(=S)$ are given, the X-ray beam can be passed through the main point a within the main plane at the angle α to a vertical line, and projected on the I—I section 16 and the FC unit 21 along the X-ray receiving direction. If $\alpha1=\alpha2=\alpha=0$ is given, moreover, then the path of the X-ray beam will be substantially normal to the main axis of the apparatus.

According to the X-ray photography apparatus of this invention, as described above, the first to fifth photographing methods can be executed by means of a single apparatus, and switching between the cine-filming and the direct photographing by means of the FC unit can be done with ease. Since the range of movement of the first and second traveling support frames 37 and 38 may fully cover the half length of the stature of a patient, moreover, various parts of the patient of the upper half and the low half of the body can be X-rayed respectively without moving the patient. Thus, X-ray photography can easily be practiced with combined use of various instruments and apparatus, such as a catheter and its associated appliances.

Although an illustrative embodiment of this invention has been described herein, the invention is not limited to the embodiment, and various changes and modifications may be effected therein by one skilled in the art without departing from the scope or spirit of the invention. In the above-mentioned embodiment, the apparatus is suspended from the ceiling 25. Alternatively, however, the apparatus may be designed as to be slidden on guide rails laid on a floor. Further, the mechanisms to reduce the rotation speeds of the motors 48, 57, 148 and 157 of FIGS. 2 and 9 and to transmit the rotatory forces of the motors to the spur gears in mesh with the fixed and movable racks may be of any other types, e.g., linear-motor type. It is to be understood, moreover, that the control circuits of FIGS. 21A and 21B may be replaced with more sophisticated position control circuits or digital computing circuits.

What we claim is:

1. An X-ray photography apparatus comprising:
  a rotating body rotatable about a substantially horizontal main axis;
  an X-ray tube for radiating an X-ray beam along a main plane containing said main axis;
  an image receiving device for photographing an X-ray image formed after the X-ray beam is transmitted through a subject lying in the path of the X-ray beam;
  first transfer means capable of supporting said image receiving device in a position off said main axis and moving said image receiving device substantially parallel to said main axis over a range exceeding the half length of the stature of the subject;
  second transfer means capable of supporting said X-ray tube substantially on the opposite side of said main axis to said image receiving device and moving said X-ray tube substantially parallel to said main axis over a range exceeding the half length of the stature of the subject;
  first tilting means attached to said first transfer means to change the direction of said image receiving device within said main plane;
  second tilting means attached to said second transfer means to change the direction of said X-ray tube within said main plane; and
  means capable of driving said first and second transfer means and said first and second tilting means to set independently the position and direction of said X-ray tube within said main plane and the position and direction of said image receiving device within said main plane.

2. The X-ray photography apparatus according to claim 1, wherein each of said first and second transfer means includes an arm protruding from said rotating member along said main axis, a traveling support frame moving along said arm and fitted with said image receiving device at the distal end portion thereof, a fixed rack fixed to said arm and extending along said main axis, a spur gear attached to said traveling support frame and in mesh with said fixed rack, a motor attached to said traveling support frame, and a reduction gear mechanism for transmitting the rotation of said motor to said spur gear.

3. The X-ray photography apparatus according to claim 2, wherein each of said first and second tilting means includes a movable rack supported on said traveling support frame so as to be movable along said main axis and having a pin fixed to the distal end portion thereof, a tilting member having a pair of guide rails, pivotally supported on said traveling support frame, capable of rotating as said movable rack moves along said main axis, and fitted with said image receiving device, said pair of guide rails being capable of engaging said pin, a spur gear in mesh with said movable rack, a motor attached to said traveling support frame, and a reduction gear mechanism for transmitting the rotation of said motor to said spur gear.

4. The X-ray photography apparatus according to claim 3, wherein said image receiving device includes a photographying unit using a film changer, a cine photographing unit, and a conversion unit for selectively using said two photographing units.

5. The X-ray photography apparatus according to claim 4, wherein said conversion unit includes means for correcting the positions of both said photographing units so that the X-ray beam may be incident substantially upon the center of a film of the film changer and that the magnification of an X-ray image obtained is substantially the same as that for the case of cine photographing by said cine photographing unit when the cine photographing is switched to the photographing using the film changer.

6. The X-ray photography apparatus according to claim 3, further comprising means for rotating said rotating body about a substantially vertical axis, means for vertically moving said rotating body, and means for moving said rotating body in a predetermined direction.

7. The X-ray photography apparatus according to claim 2, further comprising a first cable connected at one end with said first transfer means, said first tilting means, and said image receiving device and extending to the outside of said apparatus, a second cable connected with said second transfer means, said second tilting means, and said X-ray tube and extending to the outside of said apparatus, and a cable smoothing device for both said cables, said cable smoothing device including two guide bars extending parallel to each other between said two arms, two slide blocks guided by said two guide bars in sliding, a pair of pulleys curving said two cables extending along said first and second traveling support frames, respectively, at approximately 90° toward said main axis, two clamps for fixing said cables curved by said pulleys to said slide blocks, respectively, and a constant-load spiral spring coupled between said two slide blocks and functioning so that said cables curved by said pulleys are always pulled at right angles to said main axis.

* * * * *